(12) United States Patent
Argentine

(10) Patent No.: US 7,708,163 B2
(45) Date of Patent: May 4, 2010

(54) CONSTANT FORCE MATERIAL DELIVERY SYSTEM AND METHOD

(75) Inventor: Jeffery C. Argentine, Petaluma, CA (US)

(73) Assignee: Trivascular2, Inc., Santa Rosa, CA (US)

( * ) Notice: Subject to any disclaimer, the term of this patent is extended or adjusted under 35 U.S.C. 154(b) by 1079 days.

(21) Appl. No.: 11/360,077

(22) Filed: Feb. 23, 2006

(65) Prior Publication Data

US 2006/0186143 A1      Aug. 24, 2006

Related U.S. Application Data

(60) Provisional application No. 60/656,774, filed on Feb. 24, 2005.

(51) Int. Cl.
*B67B 7/00* (2006.01)

(52) U.S. Cl. ............................ 222/1; 222/325; 222/326; 222/327; 222/336; 222/386; 604/134; 604/135; 604/152

(58) Field of Classification Search ................. 222/336, 222/325, 326–327, 183, 386, 1; 604/131, 604/134, 135, 152
See application file for complete search history.

(56) References Cited

U.S. PATENT DOCUMENTS

| | | |
|---|---|---|
| 4,381,006 A | 4/1983 | Genese |
| 4,430,079 A | 2/1984 | Thill et al. |
| 4,681,566 A | 7/1987 | Fenton, Jr. et al. |
| 4,755,172 A * | 7/1988 | Baldwin ..................... 604/131 |
| 4,863,429 A | 9/1989 | Baldwin |
| 5,380,287 A | 1/1995 | Kikuchi et al. |
| 5,599,309 A * | 2/1997 | Marshall et al. ............. 604/136 |
| 5,722,956 A | 3/1998 | Sims et al. |
| 5,919,167 A * | 7/1999 | Mulhauser et al. .......... 604/131 |
| 5,954,695 A * | 9/1999 | Sims et al. .................. 604/131 |
| 6,019,747 A | 2/2000 | McPhee |
| 6,270,479 B1 * | 8/2001 | Bergens et al. .............. 604/156 |
| 6,278,892 B1 | 8/2001 | Prince |
| 6,482,186 B1 | 11/2002 | Douglas et al. |
| 6,520,937 B2 | 2/2003 | Hart et al. |
| 6,610,033 B1 | 8/2003 | Melanson et al. |
| 6,620,125 B1 | 9/2003 | Redl |
| 2003/0088262 A1 | 5/2003 | Bonnette et al. |
| 2003/0088263 A1 | 5/2003 | Bonnette et al. |
| 2004/0210130 A1 | 10/2004 | Prince |

FOREIGN PATENT DOCUMENTS

WO      WO 89/11310      11/1989

* cited by examiner

*Primary Examiner*—Frederick C. Nicolas
(74) *Attorney, Agent, or Firm*—Hoffmann & Baron, LLP

(57) ABSTRACT

Systems, devices, and methods are provided for dispensing material from a container. Devices can include driving arrangement for providing one or more forces, and actuator for activating the driving arrangement whereby the driving arrangement causes material to be dispensed from the container.

18 Claims, 11 Drawing Sheets

CONSTANT FORCE MATERIAL DELIVERY SYSTEM AND METHOD

CROSS-REFERENCE TO RELATED APPLICATIONS

This application claims the benefit of U.S. Provisional Application No. 60/656,774, filed Feb. 24, 2005, the content of which is incorporated herein by reference in its entirety.

FIELD OF THE INVENTION

This invention relates to devices, methods, and systems for dispensing materials from container. In particular, the invention provides driving means that can provide one or more forces and actuator means for activating the driving means to dispense material such as fluid from a syringe. This invention may be used in a wide variety of applications, including industrial, domestic, and medical.

BACKGROUND OF THE INVENTION

Fluid dispensing or infusion devices exist in a variety of forms, from simple gravity feed systems to complex electronic control systems, typically which utilize sophisticated features for precise control and flexibility when delivering fluids through a syringe in, e.g., medical applications. Many systems use a stepper motor to advance a lead screw in precise increments as controlled by a microprocessor, which in turn advances a plunger to deliver the fluid out of the syringe container.

Traditionally, some dispensing devices have included spring mechanisms whereby a user can apply a force to a syringe plunger. In some devices, the force applied to the syringe depends on the size of the syringe. One version of a mechanical syringe-based fluid dispensing system includes one or more constant force coil springs as the means by which fluid is driven out of the syringe container. Examples of such systems are taught in, e.g., U.S. Pat. Nos. 4,430,079; 4,681, 566; 4,863,429; 5,380,287 and 6,278,892.

What is needed, however, is a system that can reliably and simply provide specific material delivery profiles, for example, by sequentially providing two different forces to dispense material from a container. For example, when introducing materials or fluids into certain medical implants such as balloons or inflatable grafts for treating, e.g., aortic aneurysms, it is desirable to have improved methods, devices, and systems that are capable of accurately, safely and reliably delivering such materials or fluids therein. It is further desirable to have improved approaches for delivering curable materials through a catheter to such an implant under a specific force profile, such that the material can appropriately cure and thus the potential of malfunction, disfiguration, or over inflation of the graft due to improper delivery of the curable material is minimized.

BRIEF SUMMARY OF THE INVENTION

In one aspect, the present invention provides a method for dispensing a material from a container. The method can include providing a driving arrangement that is adaptable between a first configuration and a second configuration, executing a first actuation of an actuator assembly to cause the driving arrangement to assume the first configuration such that the driving arrangement forces material from the container under a first force, and executing a second actuation of the actuator assembly to cause the driving arrangement to assume the second configuration such that the driving arrangement forces material from the container under a second force. In some embodiments of the present invention, the first force is greater than the second force. The driving arrangement can include a first force generation element and a second force generation element such that when the driving arrangement is in the first configuration, both the first and the second force generation elements cause the driving arrangement to force material from the container under the first force, and when the driving arrangement is in the second configuration, only the first force generation element causes the driving arrangement to force material from the container under the second force. In some embodiments, the first force generation element can include a first spring and the second force generation element comprises a second spring. In related embodiments, the first spring can include a first leaf spring and the second spring can include a second leaf spring. In still further embodiments, the step of executing a first actuation of the actuator assembly can first controlled flow rate, and actuation of the second portion of the actuator assembly includes deactivation of the second force generation element such that when the driving arrangement is in the second configuration only the first force generation element causes the driving arrangement to force material from the container at a second controlled flow rate. In some embodiments, the material can include a fluid.

In still another aspect, the present invention provides a device that dispenses fluid from a syringe. The device can include a body that removably receives a syringe, a driving arrangement coupled with the body, where the driving arrangement is adaptable between a constrained configuration, a first active configuration, and a second active configuration. The driving arrangement can include a carriage that includes a spring support and a ram, a first spring coupled with the spring support, the first spring providing a first spring force, and a second spring coupled with the spring support, the second spring providing a second spring force. The device can also include a first actuator coupled with the driving arrangement, and a second actuator coupled with the driving arrangement. Actuation of the first actuator can release the driving arrangement from the constrained configuration to assume the first active configuration such that the first spring and the second spring transmit the first spring force and the second spring force, respectively, from the carriage ram to the syringe plunger to dispense material from a syringe chamber. Actuation of the second actuator can cause the driving arrangement to assume the second active configuration such that only the first spring transmits the first spring force from the carriage ram to the syringe plunger to dispense material from the syringe chamber. In some embodiments, the first spring force is greater than the second spring force. The first spring can include a first leaf spring and the second spring can include a second leaf spring. In some embodiments, the first actuator can include a first release member which engages and releasably secures the driving arrangement in the constrained configuration. In related embodiments, the second actuator can include a second release member which engages and releasably secures the second spring in a compressed configuration. In some embodiments, the material can include a fluid.

For a fuller understanding of the nature and advantages of the present invention, reference should be had to the ensuing detailed description taken in conjunction with the accompanying drawings. The drawings represent embodiments of the present invention simply by way of illustration. The invention is capable of modification in various respects without departing from the invention. Accordingly, the drawings and description of these embodiments are illustrative in nature, and not restrictive. For example, although the exemplary embodiments described herein are in the field of medical applications, the invention is not so limited and may be used when it is desirable to dispense material from a container in a controlled fashion.

DETAILED DESCRIPTION OF THE INVENTION

The present invention provides systems, devices, and methods for dispensing a material from a container. In one embodiment, a device includes a driving means for providing one or more forces, and an actuator means for activating the driving means. Such approaches provide for the delivery of material from a container under a constant or controlled force environment.

Examples of inflatable grafts and stent-grafts that may be utilized in conjunction with the invention disclosed herein can be found in commonly owned U.S. Pat. Nos. 6,395,019; 6,132,457; 6,331,191; 6,602,280; 6,733,521; 6,761,733 and 6,776,604 each of which is incorporated by reference herein in its entirety. Further, such examples may also be found in pending commonly owned U.S. patent application Ser. No. 10/686,863 to Chobotov et al., filed Oct. 16, 2003 and entitled "Delivery System and Methods for Bifurcated Endovascular Graft", U.S. patent application Ser. No. 10/168,053 to Murch, filed Jun. 14, 2002 and entitled "Inflatable Intraluminal Graft", U.S. patent application Ser. No. 10/461,853 to Stephens et al., filed Jun. 13, 2003 and entitled "Inflatable Implant", and U.S. patent application Ser. No. 10/384,103 to Kari et al., filed Mar. 6, 2003 and entitled "Kink-Resistant Endovascular Graft", each of which is incorporated by reference herein in its entirety.

Other applications and/or devices in which the present invention may be utilized may be found in pending, commonly-owned U.S. patent application Ser. No. 10/691,849 to Chobotov et al., filed Oct. 22, 2003 and entitled "Endoluminal Prosthesis Endoleak Management" and U.S. patent application Ser. No. 10/769,532 to Whirley et al., filed Jan. 30, 2004 entitled "Inflatable Porous Implants and Methods for Drug Delivery", each of which is incorporated by reference herein in its entirety.

Figure 1:
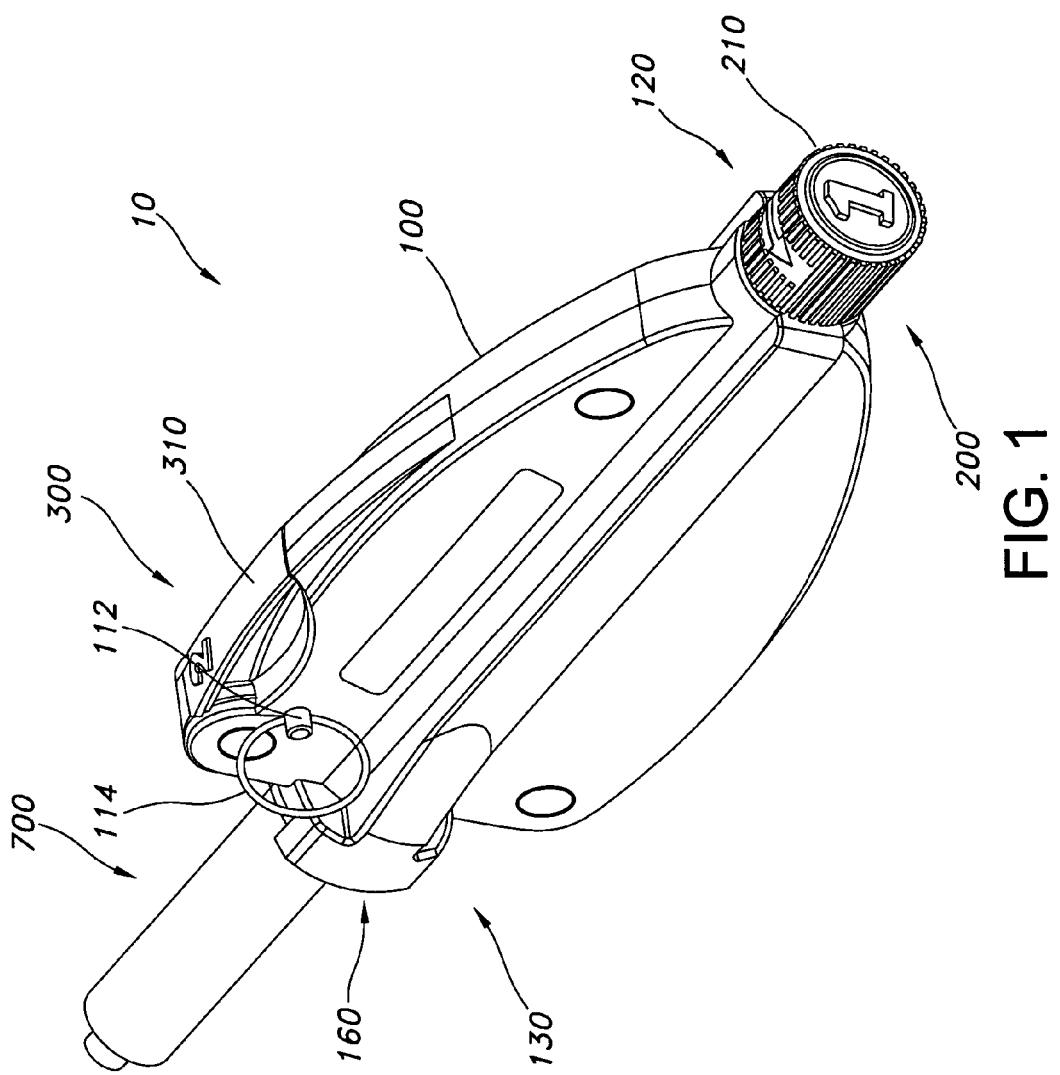
FIG. 1 is a perspective view of an exemplary device for dispensing material from a container.

Turning now to the drawings, FIG. 1 illustrates a perspective view of an exemplary device 10 for dispensing material from a container 700. Device 10 may include a body 100 having a proximal end 120 and a distal end 130. Distal end 130 may include a distal interface 160 that couples with container 700. The configuration of distal interface 160 may vary depending on the size or shape of container 700. Device 10 typically includes one or more actuators or actuator means. As shown here, device 10 includes a first actuator 200 and a second actuator 300. Second actuator release safety pin 112 and ring 114 provides a mechanism by which an operator cannot release second actuator 300 without first removing pin 112 from device body 100, as will be discussed in greater detail below. Throughout this specification, terminology such as that described above for devices is provided for illustrative rather than exhaustive purposes. Accordingly, the present invention is not meant to be limited by such descriptions.

Figure 2:
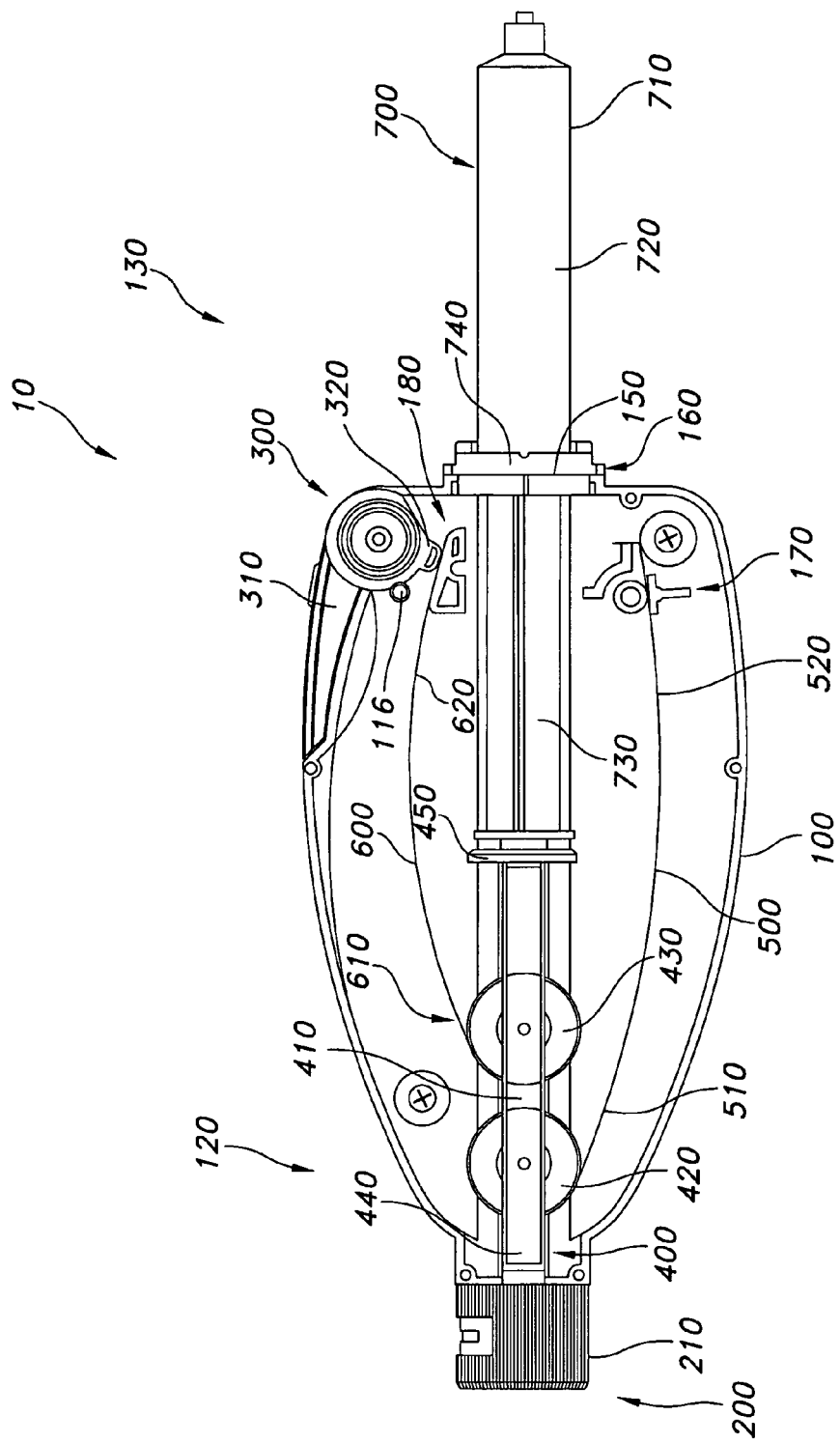
FIG. 2 is a partial cutaway elevation of the device of FIG. 1.

FIG. 2 provides a partial cut-away view of exemplary device 10. In the embodiment shown here, device 10 includes a first actuator 200 for activating a driving arrangement 400. Device 10 also includes a second actuator 300 for activating driving arrangement 400. Pin cavity 116 is adapted to receive second actuator release safety pin 112 to prevent the accidental or inadvertent release of second actuator 300. Body 100 of device 10 includes a distal opening 150 adapted to receive container 700. Container 700 in this embodiment includes a syringe 710 having a chamber 720, a plunger 730, and a flange 740. Driving arrangement 400, or driving means, which is typically at least partially housed within body 100, includes a carriage 410, a first spool 420, and a second spool 430. Carriage 410 has a proximal end 440 and a distal end 450. Body 100 may include a proximal opening 140 adapted to receive proximal end 440 of carriage 410. Driving arrangement 400 also includes a first spring 500 and a second spring 600. First spring 500 includes a proximal end 510 coupled with first spool 420, and a distal end 520 coupled with first spring mount 170 of body 100. Second spring 600 includes a proximal end 610 coupled with second spool 430, and a distal end 620 releasably coupled with second spring mount 180 of body 100.

Figure 3:
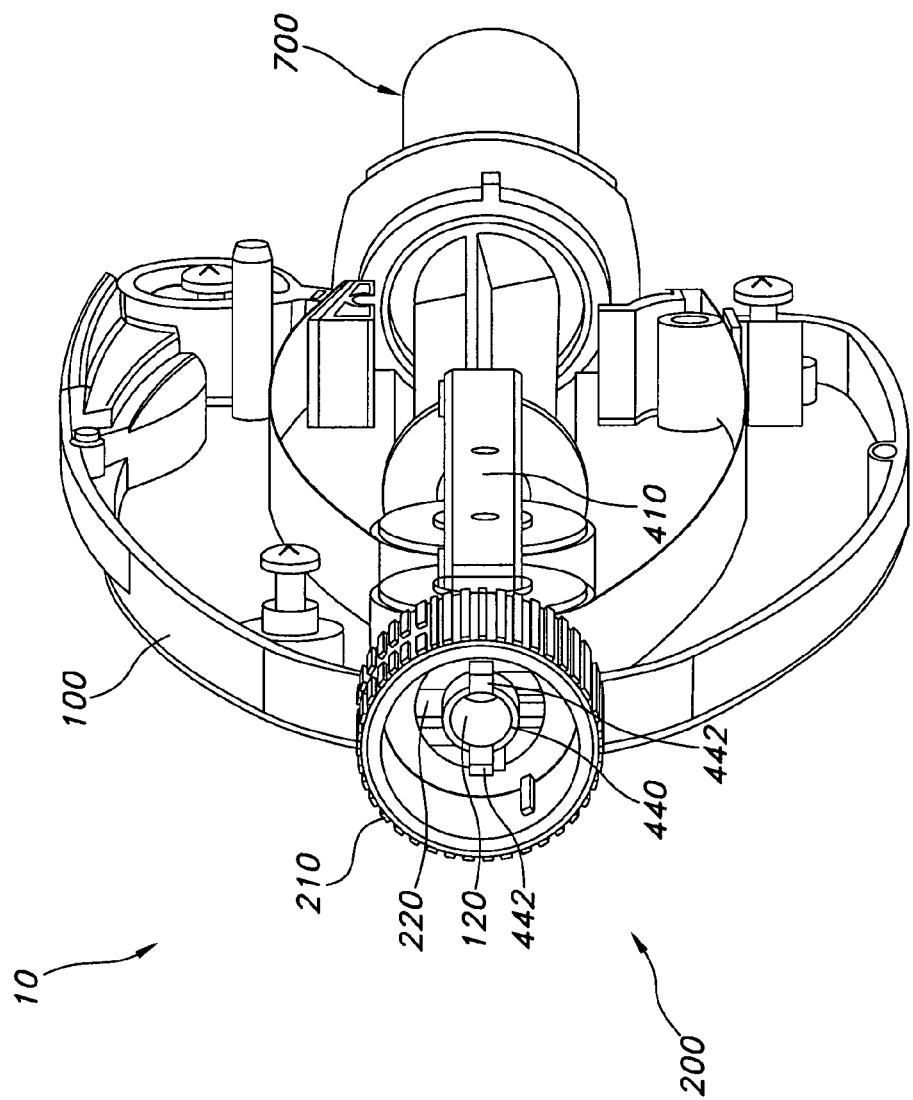
FIG. 3 is another perspective view of the device of FIG. 1 in partial cutaway.

FIG. 3 provides a partial cut-away perspective view of exemplary device 10 detailing the area around first actuator 200. As illustrated here, first actuator 200 may include a knob 210 having a keyhole-type opening 220, and proximal end 440 of carriage 410 may have key-type tabs 442 for releasably coupling with knob 210, whereby opening 220 is adapted to receive tabs 442.

Figure 4:
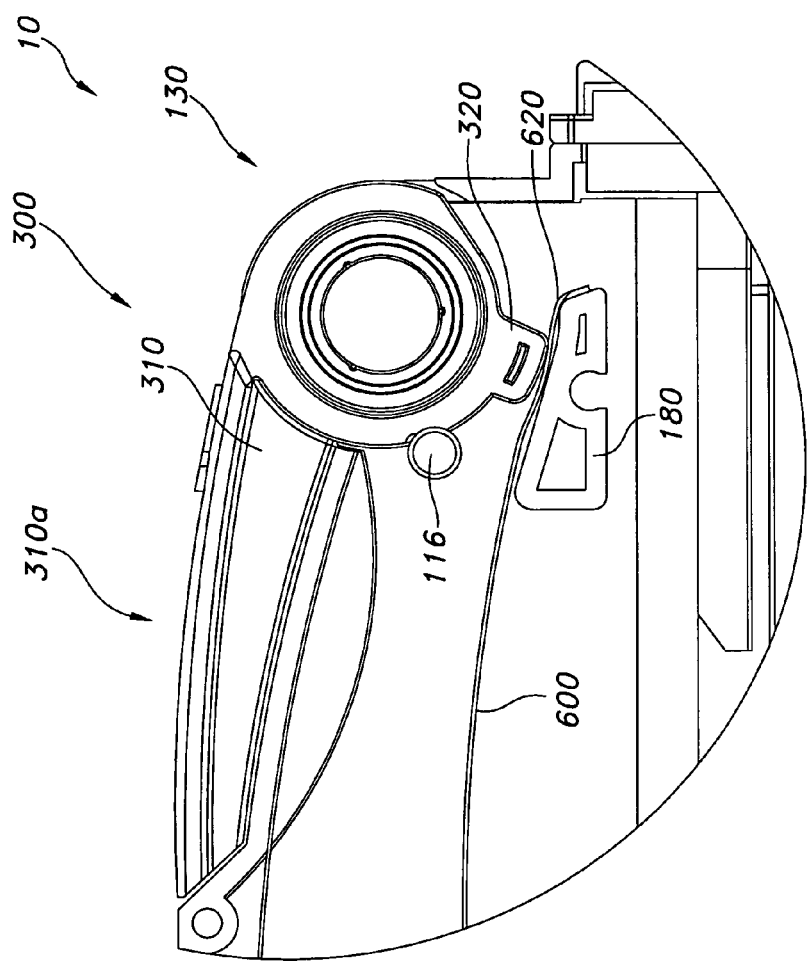
FIG. 4 is a close-up cut-away view of the device of FIG. 1 detailing a portion of the device's distal end and the area around second actuator.
Figure 5:
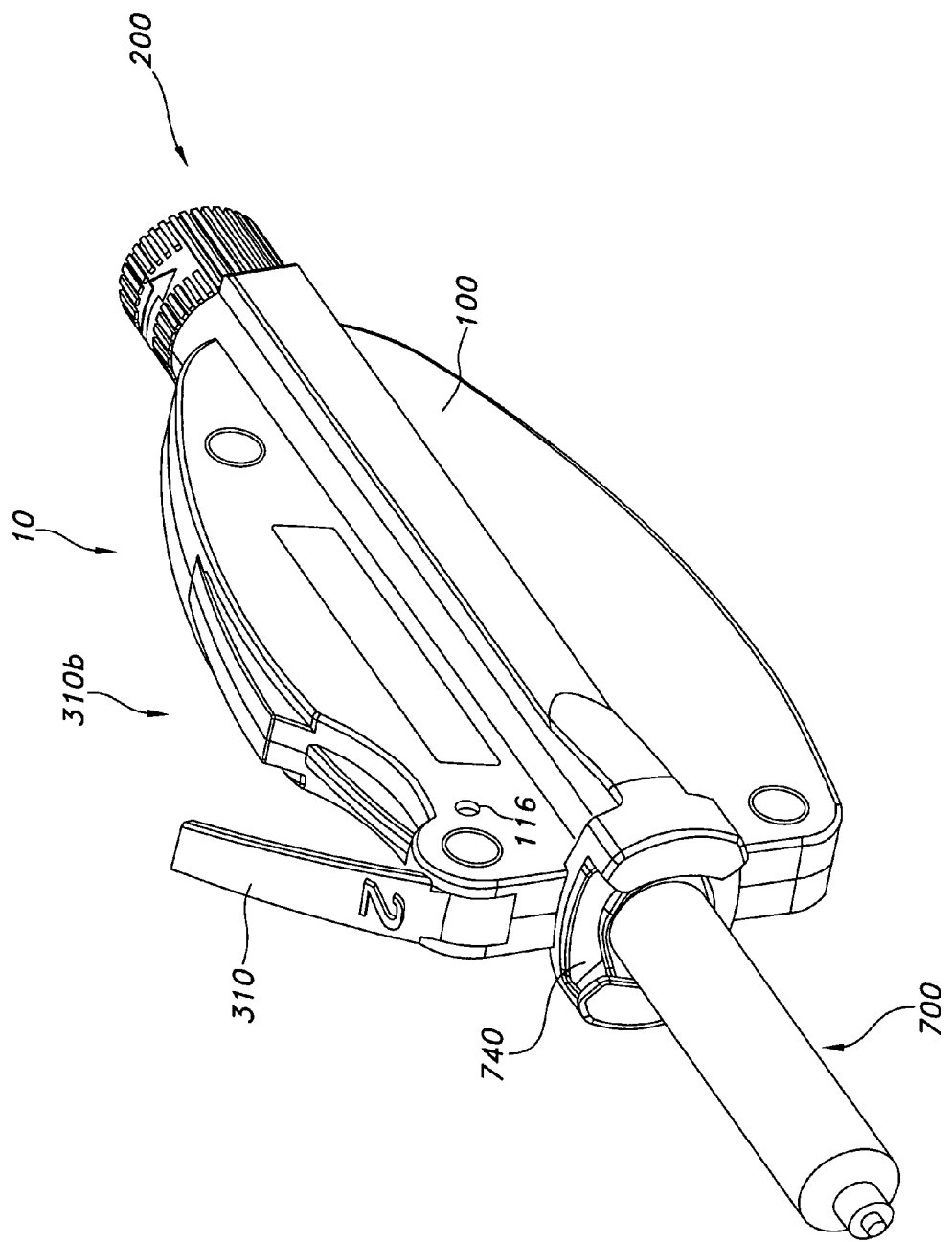
FIG. 5 is a perspective view of the device of FIG. 1, in this case with second lever shown an open or released position.
Figure 6:
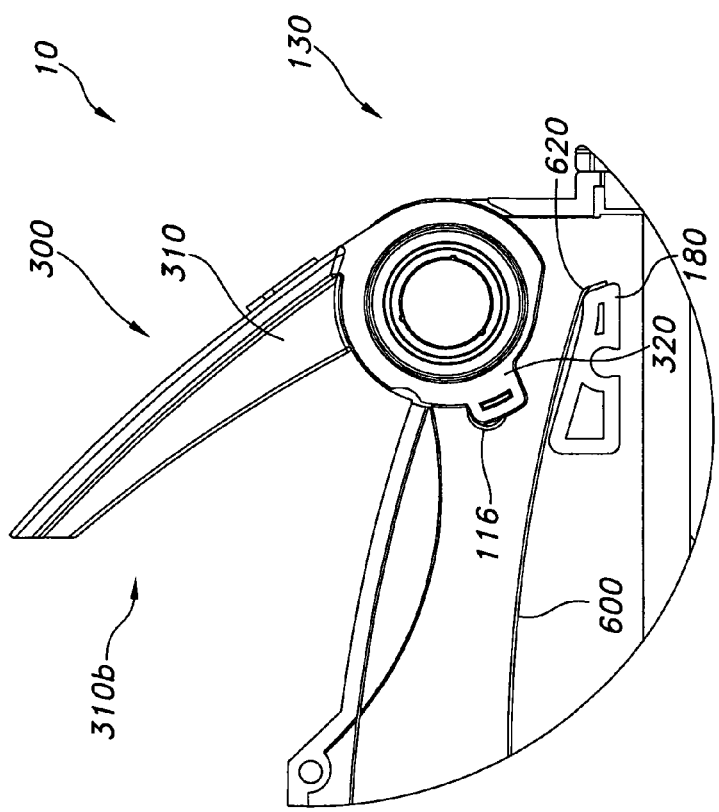
FIG. 6 is another close-up cutaway view of the device of FIG. 1, similar to that of FIG. 4, showing second lever in an open position.

FIGS. 4-6 detail the features of second actuator 300. FIG. 4 provides a close-up cut-away view of exemplary device 10 detailing a portion of the body 100 distal end 130 and, in particular, the area around second actuator 300. As shown here, second actuator 300 may include a lever 310, shown here in a closed position 310a, and a press 320 that releasably secures distal end 620 of second spring 600 against second spring mount 180.

Figure 4A:
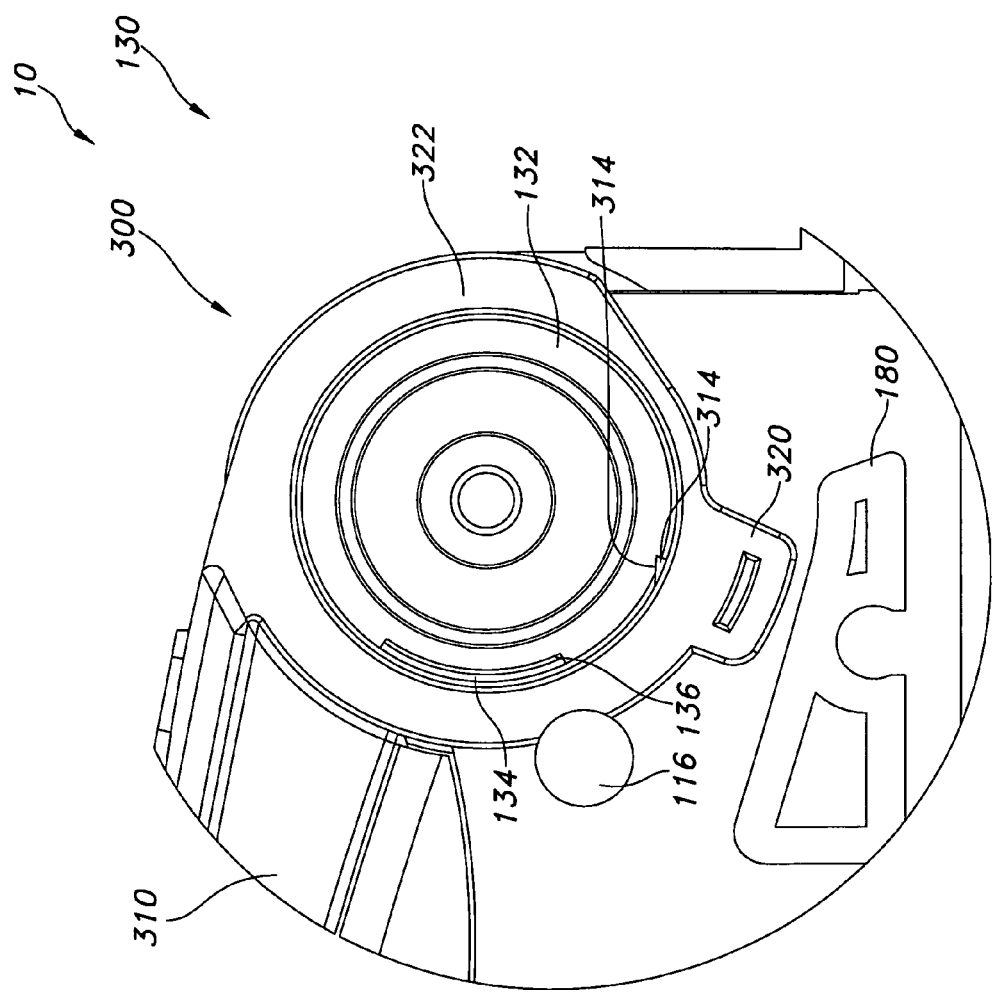
FIG. 4A is a more detailed close-up view of FIG. 4 highlighting further details of the device of FIG. 1.

FIG. 4A is a more detailed view of the area of device 10 shown in FIG. 4, again with second actuator lever 310 shown in a closed position 310a. Spring 600 has been removed for clarity. Here, a pivot boss 132 is shown as being disposed in, or as an integral part of, device body 100. Circumferential portion 322 of second actuator 300 surrounds pivot boss 132 and is free to rotate relative to pivot boss 132. Optional barb or wedge-shaped brake member 314, which in this embodiment is an integral part of second actuator 300 or circumferential portion 322, provides resistance between second actuator 300 and pivot boss 132 as the circumferential portion 322 rotates relative to pivot boss 132. As an operator lifts second actuator lever 310 and in turn causes circumferential portion 322 to rotate relative to pivot boss 132, an optional recess 134 disposed in pivot boss 132 receives barb 314, reducing the rotational resistance between circumferential portion 322 and pivot boss 132. This provides the operator with sensory feedback indicating that lever 310 has been moved to open position 310b.

Once barb 314 is in recess 134, resting interference between a raised surface 316 of barb 314 and jog surface 136 of recess 134 prevents easy rotation of second actuator lever 310 back to its original or closed position 310a, thus generally keeping second actuator lever 310 in the open position 310b and visually indicating to a user that second actuator 310 has been moved to remove second spring 600 from the force applied to dispense material from syringe chamber 720 as is described in greater detail below.

FIG. 5 is a perspective view of exemplary device 10, in this case with release safety pin 114 removed, thus revealing pin cavity 116. Lever 310 is shown here in an open or released position 310b. FIG. 6 provides another cut-away side view of exemplary device 10, detailing the area around second actuator 300, again with safety pin 114 removed and lever 310 shown in open position 310b.

Figure 7:
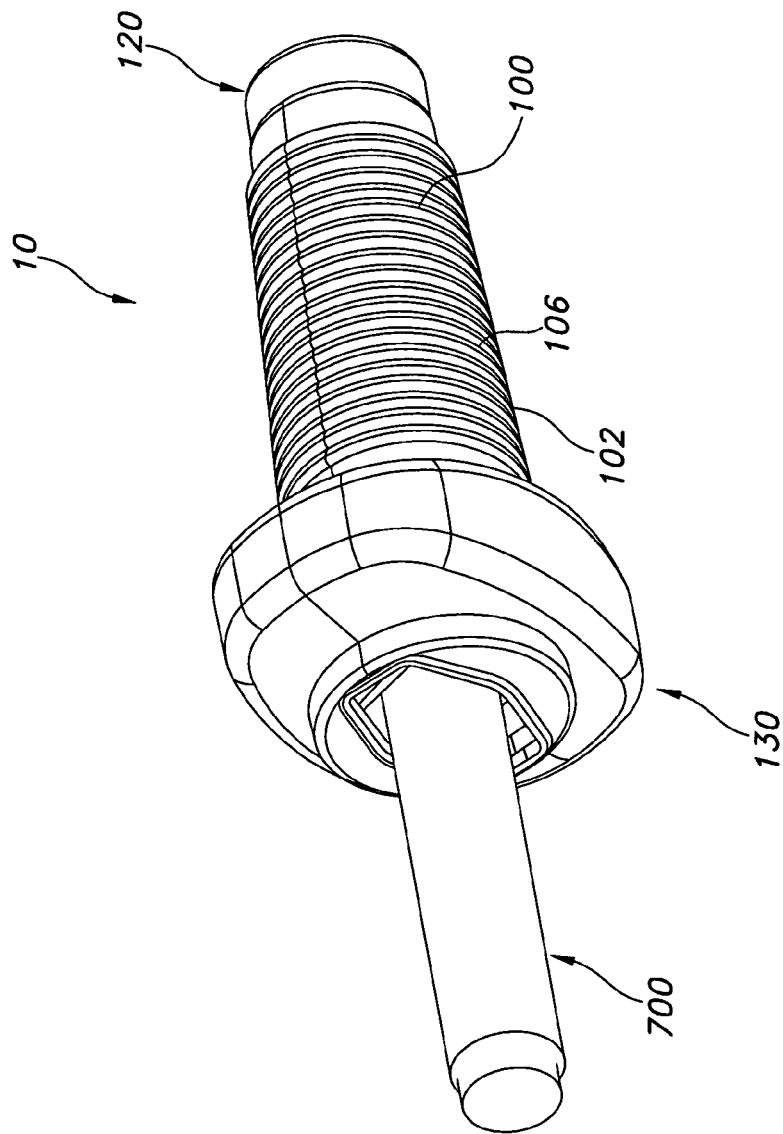
FIG. 7 is a perspective view of an alternative embodiment the device of the present invention.

FIG. 7 illustrates a perspective view of an alternative embodiment of device 10 that may be used for dispensing material under a single constant force or pressure. Here, device 10 may include a body 100 having a proximal end 120 and a distal end 130 as described above. Body 100 features a gripping surface 102 comprising optional circumferentially oriented raised projections 106 to prevent slippage of body 100 from an operator's hands.

Figure 8:
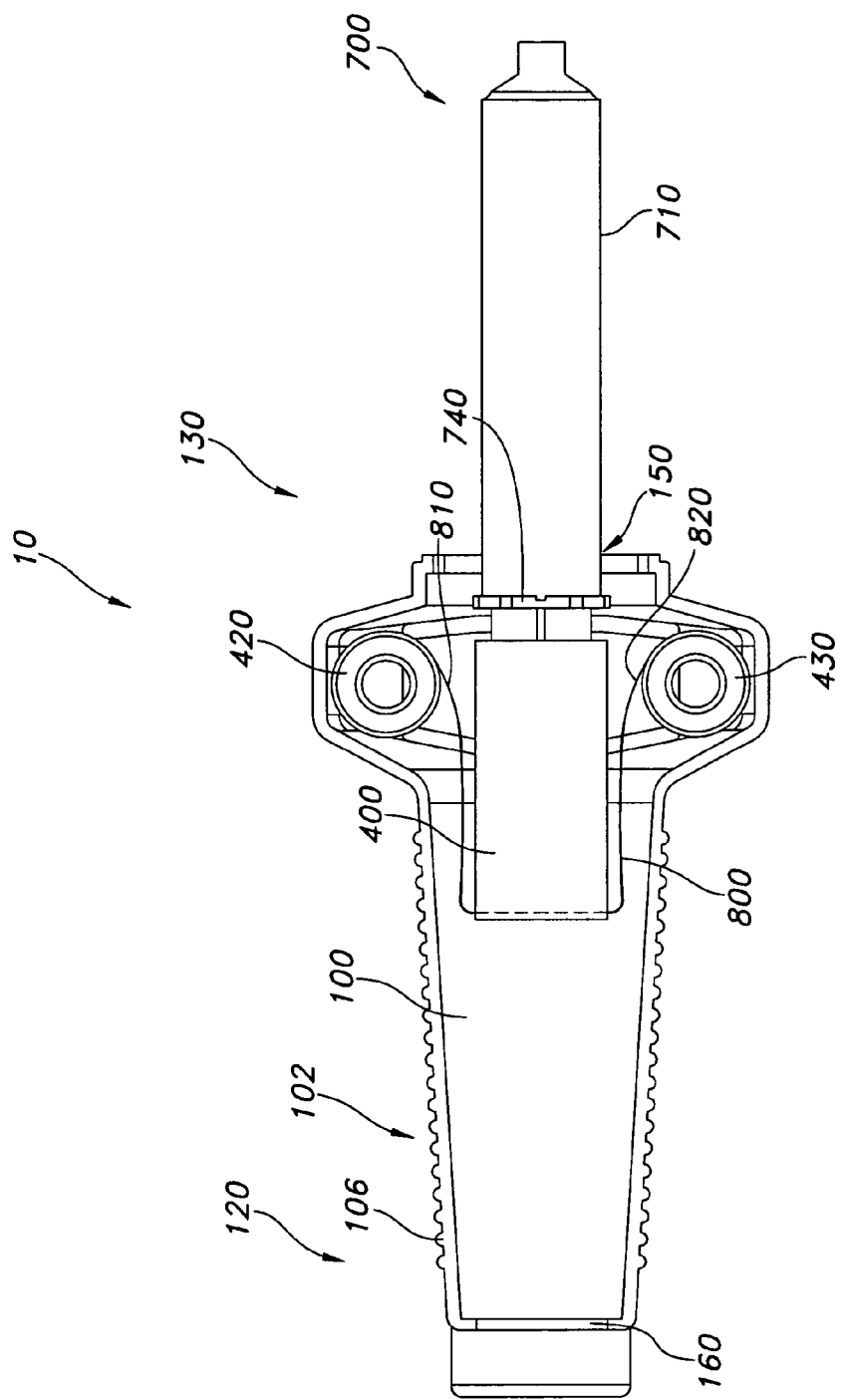
FIG. 8 is a partial cut-away view of the device of FIG. 7, detailing the configuration of its components.

FIG. 8 provides a partial cut-away view of the device of FIG. 7, detailing the configuration of its components. Body 100 of device 10 includes a distal opening 150 as described adapted to receive container 700. Container 700 may be a syringe 710 having a chamber 720, plunger 730 and flange 740 as described above. Driving arrangement 400 includes a constant force spring 800. Here, spring 800 includes a proximal end 810 coupled with a driving arrangement 400 first spool 420 and a distal end 820 coupled with a driving arrangement 400 second spool 430. Driving arrangement 400 in this embodiment also includes a carriage 410 (not shown) having a proximal end 440 and a distal end 450. In this embodiment, carriage 410 may travel along one or more rails (not shown) that are integrally formed with or attached to body 100 when spring 800 acts.

Body 100 of the embodiment of FIGS. 7-8 may, as described elsewhere herein, include distal opening 150 that is adapted to removably receive syringe 710. In operation, syringe 710 can be prepared with a desired material, and inserted through distal opening 150 such that plunger 730 contacts driving arrangement 400 and flange 740 couples or otherwise locks with distal interface 160. The embodiment of FIGS. 7-8 allows for a single step actuation of the driving arrangement 400 such that as soon as syringe 710 is loaded into device 10 as described above, driving arrangement 400 acts under the influence of constant force spring 800 to immediately drive material from syringe 710. The driving arrangement 400 may suitably be activated by a single actuator, such as the above-described first actuator 200 which may include a knob 210 or other suitable mechanism (not shown), resulting in greater ease of use, less chance for operator error. This design also affords greater stability during use due to the symmetric configuration of spring 800. Suitable activating forces include those described above.

Figure 9:
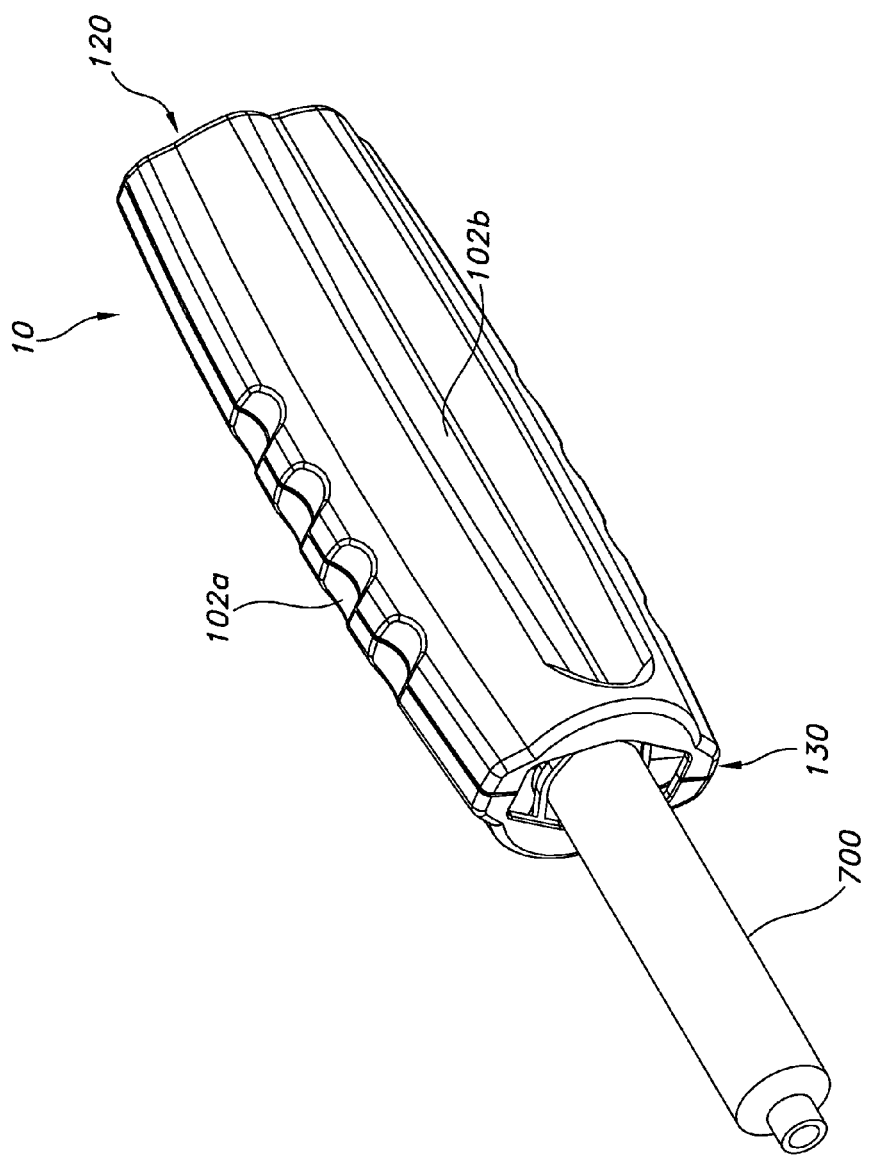
FIG. 9 is a perspective view of an alternative embodiment the device of the present invention.
Figure 10:
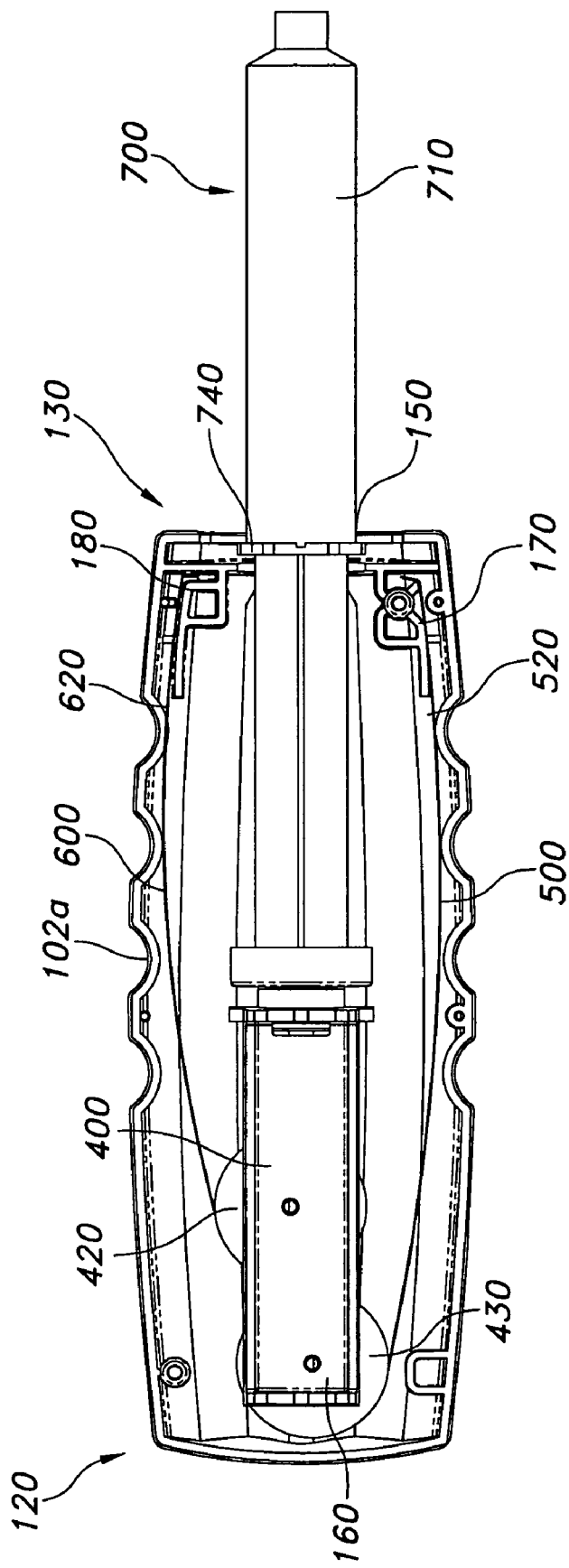
FIG. 10 is a partial cut-away view of the device of FIG. 9, detailing the configuration of its components.

FIG. 9 is a perspective view of yet another alternative embodiment of device 10, and FIG. 10 is a partial cut-away view of the device 10 of FIG. 9. As with the embodiment of FIGS. 7-8, the embodiment of FIGS. 9-10 may suitably be activated by a single actuator, such as the above-described first actuator 200 which may include a knob 210 (not shown). As depicted in FIGS. 9-10, the spools 420, 430 are arranged in series to offer a more compact or sleek configuration. The device 10 of FIGS. 9-10 may also include gripping surfaces, such as detents, including, but not limited to, finger grips 102a and/or contours or depressions 102b. Suitable activating forces include those described above.

The design of device 10, and in particular the configuration of the driving arrangement and the one or more force generation elements, affords a simple way to achieve highly controlled flow rates when dispensing material such as fluid from container 700. For instance, the driving arrangement of the present invention is capable of providing generally and relatively constant first and second forces, such as may be experienced when the force generation elements are constant force springs. The dynamic frictional and other forces inherent in device 10 and as exerted by the material or fluid as it exits container 700 tend to only nominally affect the ability of the constant force driving arrangement to deliver the material from container 700 at a constant rate.

The presence of these nominally constant driving forces also means that the material may be delivered from container 700 at a nominally constant pressure throughout the period during which material is force out of chamber 720, given the fixed geometry of the components of container 700 and accounting for the fact that typical constant force springs, for instance, may exhibit slight but measurable decrease in the force output as they extend). In particular, a first actuation of the actuator assembly will therefore cause driving arrangement 400 to force material from container 700 under a first controlled pressure, and the second actuation of the actuator assembly can cause driving arrangement 400 to force material from the container under a second controlled pressure. As discussed above, the first controlled pressure may be greater than, less than or equal to the second controlled pressure.

When introducing curable polymer materials into an inflatable graft for treating an aortic aneurysm, for instance, it is often desirable to do so under a relatively accurate, reliable, and constant pressure delivery profile to avoid complications such as graft failure. Device 10 as described herein has the ability to deliver such polymers under a controlled or constant pressure protocol and is thus a useful choice for such applications.

Therefore, although the term "constant" is used to describe various features of the present invention, it is understood that the parameters such as force, pressure and rate used herein in conjunction with this term may fluctuate somewhat during use.

In operation, a container 700 may be coupled with device 10. The fluid or other material initially contained within container 700 can be dispensed from container chamber 720 by actuating the actuator means, which in turn activates the driving means and whereby the activated driving means causes the material to be dispensed from container 700. Material may be prepared in container 700 according to a variety of approaches, as discussed below, or it may simply be transferred to chamber 720 prior to being coupled with device 10 for dispensation according to the present invention. In some medical applications, for instance, container 700 may be coupled with a catheter (not shown) to deliver material from chamber 720 to specific locations in a mammalian body (e.g., delivering an embolic composition to a duct or body lumen) or to medical devices, such as balloons or grafts, either prior to, during, or after such medical devices have been introduced into a mammalian body (e.g., delivering a curable polymer composition into an inflatable graft to treat an aortic aneurysm).

In one operative embodiment of the present invention, driving arrangement 400 may be adaptable between a first configuration and a second configuration. Execution of a first actuation of an actuator assembly causes driving arrangement 400 to assume the first configuration such that driving arrangement 400 forces material from container 700 under a first force. Further, execution of a second actuation of the actuator assembly causes driving arrangement 400 to assume the second configuration such that driving arrangement 400 forces material from container 700 under a second force. In some embodiments, the first force may be greater than the second force. In other embodiments, the first force may be equal to or less than the second force.

In a related embodiment, driving arrangement 400 may include a first force generation element and a second force generation element such that when driving arrangement 400 is in the first configuration, both the first and the second force generation elements cause driving arrangement 400 to force material from container 700 under the first force, and when driving arrangement 400 is in the second configuration, only the first force generation element causes driving arrangement 400 to force material from the container under the second force. In some embodiments, the first force generation element can include a first spring 500, and the second force generation element can include a second spring 600. In related embodiments, first spring 500 can include a first leaf spring, and second spring can include a second leaf spring. Other types of force generation elements, such as stepper motors, a series of concentric springs, etc. may be used in device 10.

In some operative embodiments, execution of a first actuation of the actuator assembly can include actuation of a first portion of the actuator assembly, and execution of a second actuation of the actuator can include actuation of a second portion of the actuator assembly. In related embodiments, execution of a first actuation of the first portion of the actuator assembly can include activation of a first force generation element and a second force generation element such that when driving arrangement 400 is in the first configuration, both the first and the second force generation elements cause driving arrangement 400 to force material from container 700 at a first controlled flow rate, and execution of a second actuation of the second portion of the actuator assembly can include deactivation of the second force generation element such that when driving arrangement 400 is in the second configuration only the first force generation element causes driving arrangement 400 to force material from container 700 at a second controlled flow rate.

In another embodiment, device 10 can include a body 100 that can removably receive container 700. In some embodiments, container 700 can include syringe 710, and body 100 can include distal opening 150 that is adapted to removably receive syringe 710. In operation, syringe 710 can be prepared with a desired material, and inserted through distal opening 150 such that plunger 730 contacts driving arrangement 400 and flange 740 couples or otherwise locks with distal interface 160.

Device 10 can include one or more actuators to actuate dispensation of material from container 700. For example, actuation of first actuator can cause driving arrangement 400 to release from the constrained configuration and to assume the first active configuration such that driving arrangement 400 transmits a first force to plunger 730 of syringe 710 to dispense material from syringe chamber 720. Actuation of second actuator can cause driving arrangement 400 to assume the second active configuration such that driving arrangement 400 transmits a second force to plunger 730 of syringe 710 to dispense material from syringe chamber 720. The configuration of distal opening 150 and distal interface 160 may vary depending on the size or shape of syringe 710. For example, distal opening 150 can be adapted to receive a 20 ml or 30 ml syringe. However, the present invention may be adapted to receive any size syringe. For example, useful, but non-limiting, syringe sizes include from about 1 ml to about 250 ml, desirably from about 3 ml to about 100 ml, more desirably from about 10 ml to about 60 ml. Particularly useful syringe sizes may be from about 20 ml to about 60 ml, including sizes from about 20 ml to about 30 ml. Syringes that work particularly well with the devices of the present invention are manufactured by Beckon, Dickinson & Co. of Franklin Lakes, N.J.

In some embodiments, driving arrangement 400 can be coupled with body 100 such that driving arrangement 400 is adaptable between a constrained configuration, a first active configuration, and a second active configuration. Carriage 410 of driving arrangement 400 can have a distal end ram 450 and a spring support which can include first spool 420 and second spool 430. First spring 500 can be coupled with first spool 420 and can provide a first spring force, and second spring 600 can be coupled with second spool 430 and can provide a second spring force. Device 10 can also include a first actuator and a second actuator, both coupled with driving arrangement 400. Actuation of first actuator can release driving arrangement from the constrained configuration to assume the first active configuration such that first spring 500 and second spring 600 transmit the first spring force and the second spring force, respectively, from carriage ram 450 to syringe plunger 730 to dispense material from syringe chamber 720. Actuation of the second actuator can cause driving arrangement 400 to assume the second active configuration such that only first spring 500 transmits the first spring force from carriage ram 450 to syringe plunger 730 to dispense material from syringe chamber 720.

Although the embodiments described thus far contemplate that first spring 500 and second spring 600 are constant or substantially constant force springs, in other embodiments one or more of the springs may be configured to provide a non-constant or variable force profile.

The first actuator can include a first release member such as knob 210 that can engage and releasably secure driving arrangement 400 in the constrained configuration. In some embodiments, knob 210 can include keyhole-type opening 220 that is adapted to receive key-type tabs 442 of driving arrangement 400. In the constrained configuration, knob 210 is rotatably positioned in a closed position 210*a* such that tabs 442 cannot pass through opening 220. Upon appropriate rotation of knob 210 to an open position 210*b*, tabs 442 can release from knob 210 and pass through opening 220 so as to release carriage 410. Release of carriage 410 allows first spring 500 and second spring 600 to act on carriage 410, causing carriage 410 to travel in a distal direction. In this way, driving arrangement 400 assumes the first active configuration. Thus, first spring 500 and second spring 600 can transmit the first spring force and the second spring force, respectively, from driving arrangement 400 to syringe plunger 730 to dispense material from syringe chamber 720.

The second actuator can include a second release member such as lever 310 that can engage and releasably secure second spring 600 in a compressed configuration. In some embodiments and as shown in FIGS. 2, 4, 4A and 6, lever 310 can include press 320 that releasably secures distal end 620 of second spring 600 against second spring mount 180. If present, optional pin 114 is removed from pin cavity 116 to allow press 320 to freely rotate upon actuation of lever 310. Subsequently, actuation of lever 310 from a closed position 310a, which holds distal end 620 against second spring mount 180, to an open position 310b, which releases distal end 620 from spring mount 180, effectively can allow driving arrangement to change from the first active configuration to the second active configuration. In this configuration, only first spring 500 transmits the first spring force from driving arrangement 400 to syringe plunger 730 to dispense material from syringe chamber 720.

Often, the second actuator is actuated at a specific time point during a material dispensing procedure. For example, lever 310 can be actuated approximately 5 minutes after knob 210 is actuated. In some embodiments, the first active configuration may provide between about 8 and about 10 pounds of force; more particularly about 8.75 pounds of force, from driving arrangement 400 to plunger 730. Likewise, the second active configuration may provide between about 1 and 4 pounds of force; more particularly about 2.6 pounds of force, from driving arrangement 400 to plunger 730. Any desired combinations of first and second forces, which may be the same or different, ranging from 16 or fewer ounces to about 50 pounds or greater, desirably from about 1 pound of force to about 20 pounds of force, more desirably from about 1 pound of force to about 10 pounds of force, may be used with the present invention. In some embodiments, the first and second forces may be equal to reduce the force standard deviation. The present invention contemplates any number or combination of actuators, including single actuator devices, force generation elements, and active configurations so as to meet the desired delivery profile needs. For example, in some embodiments, such as that shown in FIGS. 7-8, device 10 can include only one actuator and one force generation element.

The present invention is well suited for dispensing a variety of materials, including epoxies, adhesives, polymers, biological materials such as bone pastes and tissue sealants, and any of a variety of gels, foams, powders, fluids (including both liquids and gases), cements, and the like. Classes of biomaterials useful for medical applications in conjunction with the devices and methods of the present invention are generally described in pending U.S. patent application Ser. No. 09/496,231 to Hubbell et al., filed Feb. 1, 2000 and entitled "Biomaterials Formed by Nucleophilic Addition Reaction to Conjugated Unsaturated Groups," and pending U.S. patent application Ser. No. 09/586,937 to Hubbell et al., filed Jun. 2, 2000 and entitled "Conjugate Addition Reactions for the Controlled Delivery of Pharmaceutically Active Compounds", now U.S. Pat. No. 6,958,212, the contents of all of which are incorporated herein by reference. One particular application of device 10 is in dispensing a multiple-component polymer system suitable for use in a number of medical applications, such as filling body cavities or voids (e.g., fallopian tubes, blood vessels, and bile ducts), or filling inflatable medical devices (e.g., space-filling members and endovascular grafts). Particular polymeric systems useful in filling inflatable endovascular grafts are described in greater detail in pending U.S. patent application Ser. No. 10/327,711 to Chobotov et al. filed Dec. 20, 2002 and entitled "Advanced Endovascular Graft", the contents of which are incorporated herein by reference. Devices and methods for preparing such multiple-component polymers are described in greater detail in pending U.S. patent application Ser. No. 10/658,074 to Argentine et al. filed Sep. 8, 2003 and entitled "Fluid Mixing Apparatus And Method", the contents of which is hereby incorporated herein by reference.

For example, such a polymer system can be a three-component medium formed by the Michael addition process. This curable system is useful in applications in implants such as an inflatable endovascular graft and is dependent upon mixing the components in a particular sequence for a particular duration to be effective. Such a medium can include:

(1) polyethylene glycol diacrylate (PEGDA), present in a proportion ranging from about 50 to about 55 weight percent; or specifically in a proportion of about 52 weight percent, (2) pentaerthyritol tetra 3(mercaptopropionate) (QT) present in a proportion ranging from about 22 to about 27 weight percent; or specifically in a proportion of about 24 weight percent, and (3) glycylglycine buffer present in a proportion ranging from about 22 to about 27 weight percent; or specifically in a proportion of about 24 weight percent.

Variations of these components and other formulations as described in copending U.S. patent application Ser. Nos. 09/496,231 and 09/586,937, both to Hubbell et al., may be used as appropriate. In addition, PEGDA having a molecular weight ranging from about 350 to about 850 can be useful; and PEGDA having a molecular weight ranging from about 440 to about 560 can be particularly useful.

Radiopaque materials may be added to this 3-component system. Adding radiopacifiers such as barium sulfate, tantalum powder, and/or soluble materials such as iodine compounds to the glycylglycine buffer can be useful.

In the case of the use of the curable three-component PEGDA-QT-glycylglycine formulation described above in filling inflatable grafts of the type described in copending U.S. patent application Ser. No. 10/327,711 to Chobotov et al., the contents of which are incorporated herein by reference, a careful preparation and delivery protocol should be followed to ensure proper mixing, delivery, and ultimately clinical efficacy. Each of the three components is typically packaged separately in sterile containers such as syringes until the appropriate time for deploying the endovascular graft. The QT and buffer (typically glycylglycine) are first continuously and thoroughly mixed in a device such as device 10 of the present invention, typically between their respective syringes, for approximately two minutes. PEGDA is then mixed thoroughly with the resulting two-component mixture for approximately three minutes. This resulting three-component mixture is then ready for introduction into the desired inflatable graft body section as it will cure into a gel having the desired properties within the next several minutes. Cure times may be tailored by adjusting the formulations, mixing protocol, and other variables according to the requirements of the clinical setting. Details of suitable delivery protocols for these materials are discussed in U.S. patent application Ser. No. 09/917,371 to Chobotov et al., now U.S. Pat. No. 6,761,733, the contents of all of which are incorporated herein by reference It can be helpful to add an inert biocompatible material to the inflation material. For example, adding a fluid such as saline to the PEGDA-QT-glycylglycine formulation (typically after it has been mixed but before significant curing takes place) can lower the viscosity of the formulation and result in greater ease when injecting the formulation into the graft body section network of inflatable cuffs and channels without sacrificing the desired physical, chemical, and mechanical properties of the formulation or its clinical efficacy. Saline concentrations as a volume percentage of the final saline/three-component formulation combination may range from zero to as high as sixty percent or more; particularly suitable are saline concentrations ranging from about twenty to about forty percent. For example, a saline volume concentration of about thirty percent can be suitable. Alternatives to saline may include biocompatible liquids, including buffers such as glycylglycine.

Certain hydrogel polymer compositions are also useful. The hydrogel polymer can be comprised of any diamine or mixture of thereof. Desirably, the diamine or mixture thereof may be a hydrophilic diamine. The diamine monomer may be selected from polyoxyethylenediamine, triethyleneglycol diamine, polyethylene glycol diamine, di-(3-aminopropyl)diethylene glycol and combinations thereof. Desirably the polyglycidyl ether component may also be hydrophilic. The polyglycidyl ether component may be a mixture of a diglycidyl ether and a triglycidyl ether, a mixture of polyethylene glycol diglycidyl ether and trimethylolpropane triglycidyl ether, a polyethylene glycol (600) diglycidyl ether, and the like. Furthermore, the hydrogel polymer can include a radiopaque material, such as, but not limited to, sodium iodide. The diamine may be present in an amount of between about 4 to about 20 weight percent of the hydrogel polymer; and the polyglycidyl ether may be present in an amount of between about 15 to about 60 weight percent of the hydrogel polymer. Further, the diamine may be di-(3-aminopropyl)diethylene glycol; the polyglycidyl ether is a mixture of polyethylene glycol diglycidyl ether and trimethylolpropane triglycidyl ether; and the radiopaque material is selected from sodium iodide, potassium iodide, barium sulfate, Visipaque 320, Hypaque, Omnipaque 350 and Hexabrix. Such compositions are desirably flowable solution that can be delivered through the container 700. Useful, but non-limiting viscosity of the pre-cure material is between about 10 to about 500 cp (centipoise), desirably, between about 20 to about 100 cp, preferably about 30 cp. Additional details of useful flowable compositions may be found in U.S. patent application Ser. No. 10/097,467 to Whirley et al., filed Apr. 1, 2005 and entitled "A Non-Degradable, Low Swelling, Water Soluble Radiopaque Hydrogel Polymer", the contents of which are incorporated herein by reference.

This foregoing is but a few of examples of how a device 10 of the present invention can be used for a particular dispensing application. It is understood that, however, that the present device and methods may be used in a wide variety of other medical as well as non-medical applications.

The methods and devices of the present invention may be provided in one or more kits for such use. For example, the kits may include a body in operative cooperation with one or more actuators and a driving arrangement, and instructions for use. Relatedly, the kits may further include any of the other system or device components described in relation to the present invention and any other materials or items relevant to the present invention, including materials to be dispensed. The instructions for use can set forth any of the methods as described herein, and kit components can be packaged together in a pouch or a conventional surgical device packaging. Often, certain kit components will be sterilized and maintained within the kit. Optionally, separate pouches, bags, trays, or other packaging can be provided within a larger package, where the smaller packs may be opened individually to separately maintain the components in sterile fashion.

Although there is shown and described certain embodiments of the invention, this invention is not limited thereto, but may be variously embodied to practice the scope of the following claims. From the foregoing description, it will be apparent that various changes may be made without departing from the spirit and scope of the invention as defined by the following claims.

What is claimed is:

1. A method for dispensing a material from a container, the method comprising:
   providing a driving arrangement that is adaptable between a first configuration and a second configuration;
   executing a first actuation of an actuator assembly to cause the driving arrangement to assume the first configuration such that the driving arrangement forces material from the container under a first force; and
   executing a second actuation of the actuator assembly to cause the driving arrangement to assume the second configuration such that the driving arrangement forces material from the container under a second force;
   wherein the first force is greater than the second force.

2. The method of claim 1 wherein the material comprises a fluid.

3. A method for dispensing a material from a container, the method comprising:
   providing a driving arrangement that is adaptable between a first configuration and a second configuration;
   executing a first actuation of an actuator assembly to cause the driving arrangement to assume the first configuration such that the driving arrangement forces material from the container under a first force; and
   executing a second actuation of the actuator assembly to cause the driving arrangement to assume the second configuration such that the driving arrangement forces material from the container under a second force;
   wherein the driving arrangement comprises a first force generation element and a second force generation element such that when the driving arrangement is in the first configuration, both the first and the second force generation elements cause the driving arrangement to force material from the container under the first force, and when the driving arrangement is in the second configuration, only the first force generation element causes the driving arrangement to force material from the container under the second force.

4. The method of claim 3 wherein the first force generation element comprises a first spring and the second force generation element comprises a second spring.

5. The method of claim 4 wherein the first spring comprises a first leaf spring and the second spring comprises a second leaf spring.

6. A method for dispensing a material from a container, the method comprising:
   providing a driving arrangement that is adaptable between a first configuration and a second configuration;
   executing a first actuation of an actuator assembly to cause the driving arrangement to assume the first configuration such that the driving arrangement forces material from the container under a first force; and
   executing a second actuation of the actuator assembly to cause the driving arrangement to assume the second configuration such that the driving arrangement forces material from the container under a second force;
   wherein the step of executing a first actuation of the actuator assembly comprises actuation of a first portion of the actuator assembly, and the step of executing a second actuation of the actuator comprises actuation of a second portion of the actuator assembly;
   wherein the step of executing a first actuation of the first portion of the actuator assembly comprises activation of a first force generation element and a second force generation element such that when the driving arrangement is in the first configuration, both the first and the second force generation elements cause the driving arrangement to force material from the container at a first controlled flow rate, and the step of executing a second actuation of the second portion of the actuator assembly comprises deactivation of the second force generation element such that when the driving arrangement is in the second configuration only the first force generation element causes the driving arrangement to force material from the container at a second controlled flow rate.

7. A device that dispenses material from a container, the device comprising:
   a driving arrangement that is adaptable between a first configuration and a second figuration; and
   an actuator assembly coupled with the driving arrangement;
   wherein a first actuation of the actuator assembly causes the driving arrangement to assume the first configuration such that the driving arrangement forces material from the container under a first force, and a second actuation of the actuator assembly causes the driving arrangement to assume the second configuration such that the driving arrangement forces material from the container under a second force;
   wherein the first force is greater than the second force.

8. The device of claim 7 wherein the material comprises a fluid.

9. A device that dispenses material from a container, the device comprising:
   a driving arrangement that is adaptable between a first configuration and a second figuration; and
   an actuator assembly coupled with the driving arrangement;
   wherein a first actuation of the actuator assembly causes the driving arrangement to assume the first configuration such that the driving arrangement forces material from the container under a first force, and a second actuation of the actuator assembly causes the driving arrangement to assume the second configuration such that the driving arrangement forces material from the container under a second force;
   wherein the driving arrangement comprises a first force generation element and a second force generation element such that when the driving arrangement is in the first configuration, both the first and the second force generation elements cause the driving arrangement to force material from the container under the first force, and when the driving arrangement is in the second configuration, only the first force generation element causes the driving arrangement to force material from the container under the second force.

10. The device of claim 9 wherein the first force generation element comprises a first spring and the second force generation element comprises a second spring.

11. The device of claim 10 wherein the first spring comprises a first leaf spring and the second spring comprises a second leaf spring.

12. A device that dispenses material from a container, the device comprising:
   a driving arrangement that is adaptable between a first configuration and a second figuration; and
   an actuator assembly coupled with the driving arrangement;
   wherein a first actuation of the actuator assembly causes the driving arrangement to assume the first configuration such that the driving arrangement forces material from the container under a first force, and a second actuation of the actuator assembly causes the driving arrangement to assume the second configuration such that the driving arrangement forces material from the container under a second force;
   wherein the first actuation of the actuator assembly comprises actuation of a first portion of the actuator assembly, and the second actuation of the actuator comprises actuation of a second portion of the actuator assembly;
   wherein actuation of the first portion of the actuator assembly comprises activation of a first force generation element and a second force generation element such that when the driving arrangement is in the first configuration, both the first and the second force generation elements cause the driving arrangement to force material from the container at a first controlled flow rate, and actuation of the second portion of the actuator assembly comprises deactivation of the second force generation element such that when the driving arrangement is in the second configuration only the first force generation element causes the driving arrangement to force material from the container at a second controlled flow rate.

13. A device that dispenses fluid from a syringe, the device comprising: a body that removably receives a syringe;
   a driving arrangement coupled with the body, where the driving arrangement is adaptable between a constrained configuration, a first active configuration, and a second active configuration, the driving arrangement comprising:
   a carriage comprising a spring support and a ram;
   a first spring coupled with the spring support, the first spring providing a first spring force; and
   a second spring coupled with the spring support, the second spring providing a second spring force;
   a first actuator coupled with the driving arrangement; and
   a second actuator coupled with the driving arrangement;
   wherein actuation of the first actuator releases the driving arrangement from the constrained configuration to assume the first active configuration such that the first spring and the second spring transmit the first spring force and the second spring force, respectively, from the carriage ram to the syringe plunger to dispense material from a syringe chamber; and
   wherein actuation of the second actuator causes the driving arrangement to assume the second active configuration such that only the first spring transmits the first spring force from the carriage ram to the syringe plunger to dispense material from the syringe chamber.

14. The device of claim 13 wherein the first spring force is greater than the second spring force.

15. The device of claim 13 wherein the first spring comprises a first leaf spring and the second spring comprises a second leaf spring.

16. The device of claim 13 wherein the first actuator comprises a first release member which engages and releasably secures the driving arrangement in the constrained configuration.

17. The device of claim 13 wherein the second actuator comprises a second release member which engages and releasably secures the second spring in a compressed configuration.

18. The device of claim 13 wherein the material comprises a fluid.

* * * * *